United States Patent [19]

Fleer et al.

[11] Patent Number: 4,874,314
[45] Date of Patent: Oct. 17, 1989

[54] SOCKET TO CLAMPINGLY HOLD DENTAL TOOLS

[75] Inventors: Ernst O. Fleer, Bensheim; Hermann Landgraf, Lorsch; Werner Schwarz, Heppenheim, all of Fed. Rep. of Germany

[73] Assignee: Siemens Aktiengesellschaft, Berlin and Munich, Fed. Rep. of Germany

[21] Appl. No.: 132,008

[22] Filed: Dec. 11, 1987

[30] Foreign Application Priority Data

Dec. 22, 1986 [DE] Fed. Rep. of Germany ....... 3644055

[51] Int. Cl.⁴ .............................................. A61C 1/14
[52] U.S. Cl. .................................... 433/129; 433/127; 279/43; 279/50
[58] Field of Search ......................... 433/127, 128, 129; 279/41 R, 46 R, 50, 43

[56] References Cited

U.S. PATENT DOCUMENTS

| 495,267 | 4/1893 | Richmond | 433/127 |
| 3,094,338 | 6/1963 | Page | 433/127 |
| 4,089,115 | 5/1978 | Heil et al. | 433/124 |
| 4,198,754 | 4/1980 | Lares et al. | 433/129 |
| 4,370,132 | 1/1983 | Wohlgemuth | 433/128 |
| 4,398,886 | 8/1983 | Schuss et al. | 433/128 |
| 4,621,960 | 11/1986 | Tollner | 279/41 R |
| 4,661,062 | 4/1987 | Seigneurin | 433/128 |

FOREIGN PATENT DOCUMENTS 0037021 10/1981 European Pat. Off. .
3402635 8/1985 Fed. Rep. of Germany .

Primary Examiner—John J. Wilson
Assistant Examiner—Adriene J. Lepiane
Attorney, Agent, or Firm—Hill, Van Santen, Steadman & Simpson

[57] ABSTRACT

A socket, which receives a tool having a cylindrical shaft and which is mounted for rotation to rotate the tool, has an outer sleeve which receives a clamping sleeve and a ram for engaging a first end of the clamping sleeve. The first end of the clamping sleeve is provided with slots defining resilient tongues which are moved from a clamping position radially outward to a position for releasing the shaft by engagement with the ram. The ram has either an outer conically tapered surface or partially conically outer tapered surfaces on projections which engage inner tapered surfaces of each of the tongues or fingers. Preferably, the tapers of the ram and fingers are selected so that only substantially a line contact is formed therebetween to reduce the force necessary to move the fingers or tongues radially outward to the declamping or disengaging position.

16 Claims, 2 Drawing Sheets

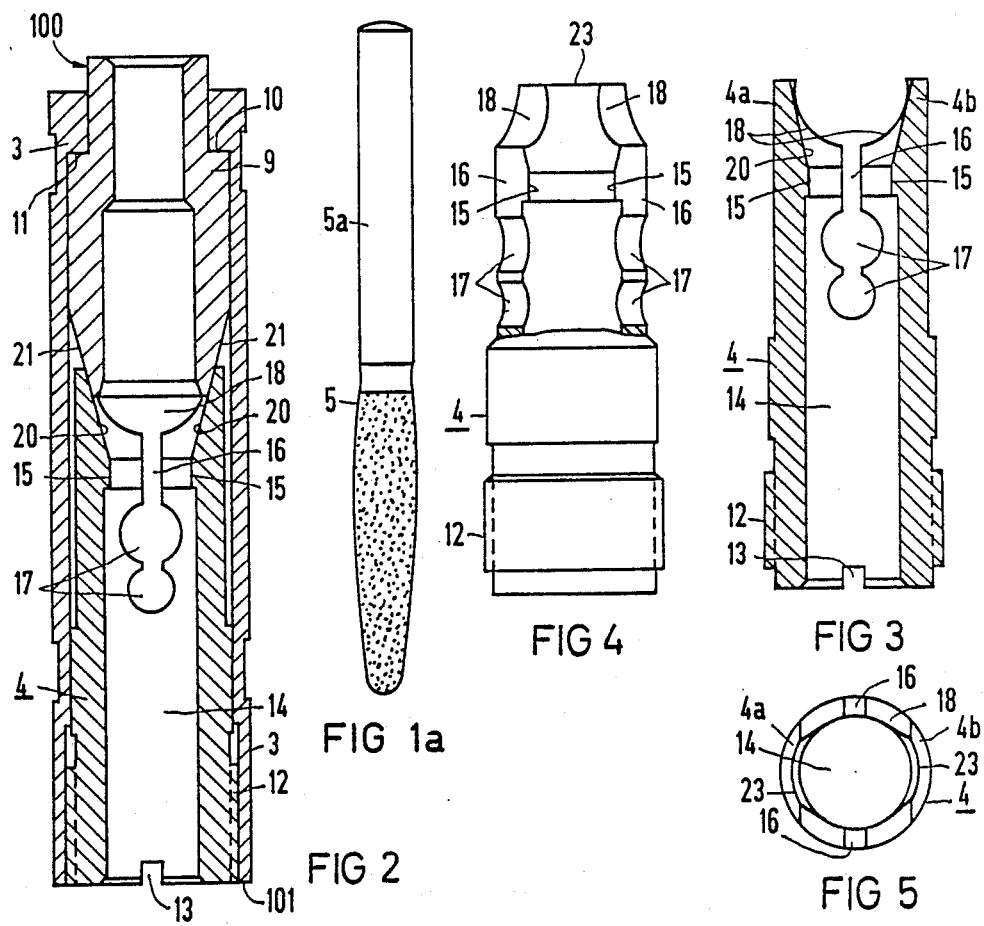

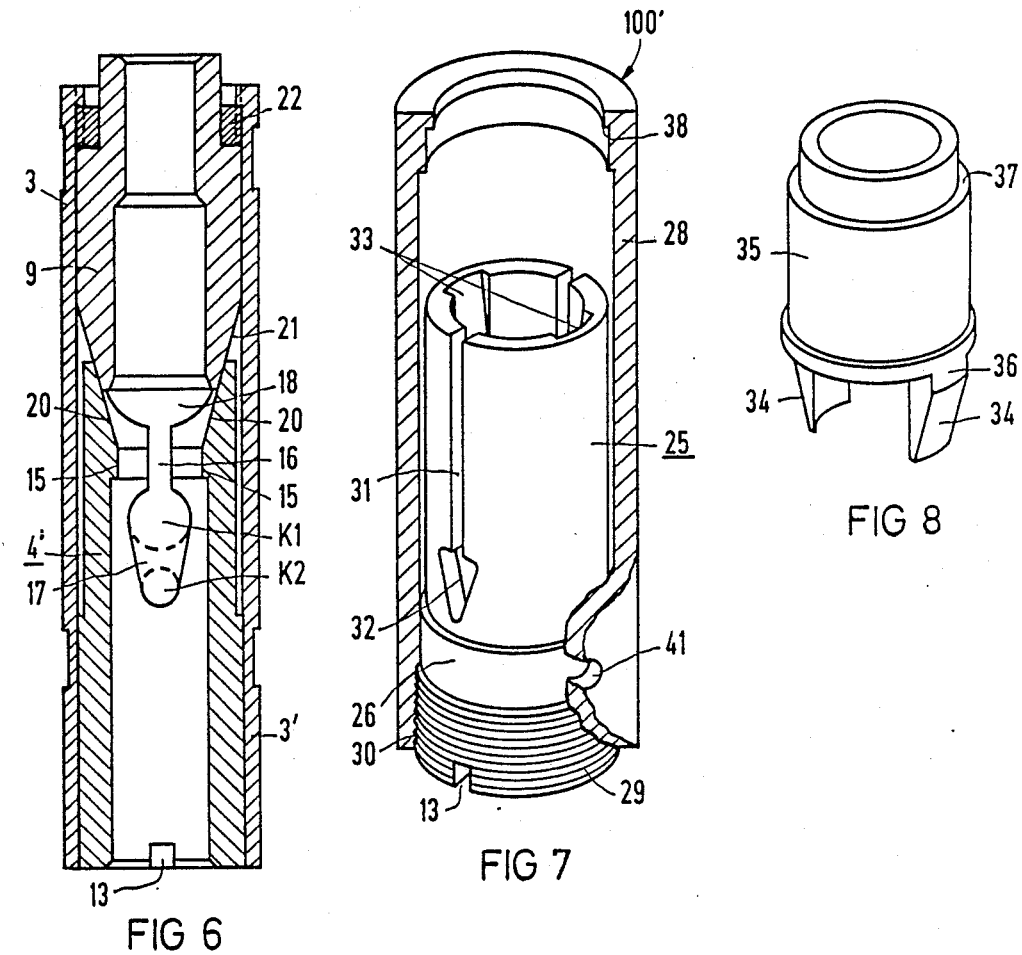
FIG 6
FIG 7
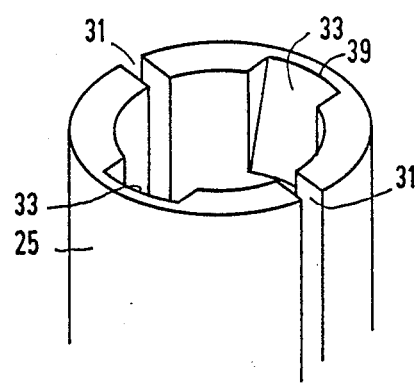
FIG 8
FIG 9

SOCKET TO CLAMPINGLY HOLD DENTAL TOOLS

BACKGROUND OF THE INVENTION

The present invention is directed to a socket having gripping means for gripping a tool having a cylindrical shaft, such as a dental tool. The socket includes a sleeve-shaped shaft which is mounted for rotation and accepts a clamping sleeve which holds a tool shaft. The clamping sleeve has at least two longitudinal slots extending inward from a first end of the clamping sleeve which faces away from the tool to form resilient tongues which are movable from a clamping position for engaging the tool shaft to an outward position to allow releasing of the shaft. The socket includes an axially movable ram, which is actuated by a handle for the purpose of moving the tongues from the clamping position to an unclamped position to allow releasing the tool, and the ram has an outside tapering conical surface for engaging the one end of the clamping sleeve which is provided with an inwardly tapering surface.

A rotary socket having a clamping sleeve for gripping a shaft of a tool is disclosed in U.S. Pat. No. 4,089,115. In this arrangement, a ram is threaded into the end of the shaft and is movable by means of a separate tool, such as a polygonal-shaped wrench or the like, from a retracted position withdrawn from engagement with the gripping sleeve to a position causing the gripping sleeve to release the tool. In the clamped position, the tool shaft is held by the clamping tongues of the clamping sleeve with a fricational grip. In a retracted position, the ram is situated at a slight axial distance from the corresponding ends of the sleeve. For removing the tool, the ram is threaded into the shaft until its outside conical end engages inside, conical surfaces of the clamping sleeve to resiliently bias the tongues radially outward to a releasing position to release the tool shaft.

Dependent on the extent on which the ram is screwed into the shaft, a certain pre-adjustment of the clamping tongues can also be achieved with this device. The two cones are in engagement with one another in this pre-adjustment on one hand, but on the other hand, a reliable holding of the tool shaft in the clamped position still is established.

A disadvantage with this clamping device is that an additional tool is required for removing a tool that is gripped in the gripping sleeve. Another significant disadvantage, moreover, is that the clamping tongues are subjected to a torsional stress when the ram is screwed in and, thus, the useful life of the clamping sleeve is reduced.

Another known type of clamping device or socket is disclosed in German OS 34 02 635. As disclosed, a pre-adjustment of the clamping tongues, such as mentioned above, is achieved in that the clamping tongues are spread by a pressure member, which is seated in an axial movable fusion in the head housing. A stop element for one-time adjustment of this pre-adjustment is allocated to this pressure member, and this stop element is positioned in various positions by means of being screwed into the shaft and limiting the movement of the pressure member from the clamping sleeve. Of the two exemplary embodiments shown in this German reference, one, likewise, has the disadvantage that relatively high forces must be exerted in order to bring the clamping sleeve out of the clamping position into an unclamped position to allow removal of the tool. The other embodiment is relatively complicated to manufacture due to the many parts of the arrangement composed of the spreader element and pressure member and, in particular, due to the spreader element with the key surfaces. Another disadvantage is that the spreader element must be integrated positionally dependent on the clamping sleeve and this makes assembly more difficult.

SUMMARY OF THE INVENTION

The object of the present invention is to provide a chuck or socket with a clamping device, which is an improvement over the prior art and which, in particular, is well-suited for push-button actuation. The improved socket has the improved possibilities of integration being established in comparison to known designs and has, insofar as possible, fewer or, respectively, less involved parts. The socket enables removal of the tool with a low exertion of force while holding the tool with high retaining forces. Over and above this, the goals of the improved socket are to be able to assemble the parts, which are positionally independent of one another.

Significant advantages of the invention over the prior art are that the clamping device is composed of a total of only three parts, that the lower number of contacting faces having a higher processing quality are present, and that the assembly can occur proceeding from the tool side. This has the advantage that the adjustment tolerances lie at the side facing away from the pressure cover and, by contrast, extremely narrow tolerances can be observed at the side of the pressure cover.

Other advantages and features of the invention will be readily apparent from the following description of the preferred embodiments, the drawings and claims.

BRIEF DESCRIPTION OF THE DRAWINGS

FIG. 1 is a cross sectional view, with portions in elevation for purposes of illustration, of a head housing of a dental turbine handpiece having the rotary socket of the present invention;

FIG. 1a is a side view of a tool received in the rotary socket of the present invention;

FIG. 2 is a longitudinal cross sectional view of a socket with the clamping arrangement of the present invention;

FIG. 3 is a longitudinal cross sectional view of the clamping sleeve removed from the socket in accordance with the present invention;

FIG. 4 is a side elevational view, with portions removed for purposes of illustration, of the clamping sleeve of FIG. 3 rotated through approximately 90°;

FIG. 5 is an end view of the clamping sleeve of FIG. 3;

FIG. 6 is a longitudinal cross sectional view similar to FIG. 2 of a modification of the clamping sleeve in accordance with the present invention;

FIG. 7 is a perspective view, with portions broken away for purposes of illustration, of an embodiment of the socket in accordance with the present invention;

FIG. 8 is a perspective view of a ram utilized with the clamping sleeve of FIG. 7;

FIG. 9 is an enlarged perspective view of an end of the clamping sleeve of FIG. 7.

DESCRIPTION OF THE PREFERRED EMBODIMENTS

The principles of the present invention are particularly useful when incorporated in a socket or chuck, generally indicated at 100 in FIG. 2. The socket 100 has an outer sleeve 3 which is connected with a rotor 2 (FIG. 1) and the sleeve and rotor are mounted in a head housing 1 of a dental handpiece having a turbine for rotation in a known manner, such as by ball bearings. The socket 100 has a clamping sleeve 4 mounted in the outer sleeve 3 for releasably holding a cylindrical shaft 5a of a tool 5 (FIG. 1a), which may be a drill, a miller or the like. As illustrated in FIG. 1, for the removal of the tool, a pressure cover 6 is arranged on an end of the head housing 1 facing away from the tool, and this pressure cover, when pushed against a compressive spring 7, has a pressure face or projection 8 that presses against a sleeve-shaped ram 9, which is axially displaceable within the outer sleeve 3. When the ram 9 is moved into engagement with a first end of the clamping sleeve 4, it will cause the clamping sleeve to release the tool to allow its removal.

The structure of the socket 100 is best illustrated in FIGS. 2-5. The outer sleeve 3 is fashioned as a sleeve structure with an inwardly extending flange forming a step or shoulder 10 at a first or one end, which is away from a second end 101 in which the tool is inserted. A ram 9 having a shoulder 11 is movable from a position illustrated in FIG. 2, with the shoulder 11 engaging the step 10 axially towards the opposite end 101. At the opposite end 101 of the sleeve 3, which is the tool entry end, the clamping sleeve 4 has its first end inserted into the outer sleeve 3 and the two sleeves are secured together, such as by having threads on the inner sleeve engaged in threads on the outer sleeve to form a screw-type connection 12 adjacent a second end of the sleeves, which is also adjacent the entry end for the tool. A slot 13 is provided on a second end of the sleeve 4 to enable engagement by a separate tool, such as a screwdriver, in order to facilitate this threading of the sleeves together.

The sleeve 4, as best illustrated in FIGS. 3 and 4, has an inside bore or diameter 14, which roughly corresponds to the diameter of the tool shaft 5a of the tool 5, which is to be received in the sleeve. In the first or the upper end facing away from the tool entry end, the inside diameter is slightly smaller than the shaft diameter of the tool to provide contact faces, such as 15, with which the clamping sleeve presses against the tool shaft 5a with a defined clamping force in this region. In order to keep the wear of the contact faces 15 and of the inside bore 14 as low as possible, the clamping sleeve is completely or partially coated with CVD. (Chemical-Vapour-Deposition)

In a known fashion, the clamping sleeve 4 has two slots 16, which extend inward from the first end and are diametrically opposite one another. Each of the slots 16 inward of the first end passes through two circular opening or apertures 17 with the slot ending in the axially spaced innermost aperture. Adjacent the first end, the slot 16 extends into a semicircular recess 18. As a result of the slot 16, the apertures 17 and recesses 18, two resilient tonges 4a and 4b are formed over the circumference of the sleeve 4, as best illustrated in FIGS. 3 and 5. These tongues 4a and 4b will press against the tool shaft 5a with the contact faces 15 when in the clamped position and are spread radially outward to an unclamping position to allow removal of the tool. The recesses 18 are, advantageously, such that the circumferential line from slot to slot decreases towards the free, first end of the tongues, and the resilient tongues become narrower towards their free, first ends, as seen in FIG. 4.

At the first end, which faces away from the second or tool entry end, the clamping sleeve 4 comprises a partial inside cone or inner tapering surface 20, which extends at approximately 18° relative to the axis of the sleeve. The cone 20 corresponds with an outside cone or outer tapering surface 21 of the ram 9. The outside cone 21 extends at approximately 30° angle with the axid and is, thus, flatter than the inside cone of the clamping sleeve. In combination with the aforementioned recess 18, the contacting between the two cones 20 and 21 is practically limited to a light contact, such as the end line 23 of the tongues, and this results in a very low disengagement force being required.

In the clamping position, the two cones 20 and 21 are in engagement with one another; however, with the insertion of the tool 5, by contrast, the two cones 20 and 21 do not contact while in the clamped position of the clamping sleeve. The tool shaft 5a is held in the clamped position via the contact faces 15. The ram is pushed against the step 10 of the shaft 3, given axial introduction of the tool. In order to cancel the retaining force and to be able to remove the tool from the clamping device, a select pressure on a pressure cover 6 is required. Pressure member or projection 8 of the cover will then be pressed against the end face of the ram 9 and further pressure will move this axially downward, as illustrated in FIG. 2, so that as a consequence the conical connection of the ram cone 21 of the ram with the cone 20 of the two clamping tongues 4a and 4b will occur. The two clamping tongues 4a and 4b will then be pressed radially outward and the retaining force on the contact faces 15 will be cancelled. After the pressure cover 6 is released, it will move back to its initial position due to the force of the spring 7. The ram 9 is again pressed against the detent or stop surface 10 due to a consequence of the force components acting parallel to the axis, which occur due to the slanting surfaces of the cone faces.

Since the ram 9 is a rotationally symmetrically turned part, it is very easy to manufacture during an automated manufacturing process. Since the insertion of the ram 9 into the sleeve 3 is positionally independent, an assembly of the ram is very simple. First, the ram 9 is axially introduced into the sleeve 3 from the second end or tool side 101. Subsequently, the clamping sleeve 4 is inserted and threaded to form the thread connection 12 with the depth of the thread connection defining the degree of pre-adjustment for the tongues 4a and 4b relative to the ram 9.

A modification of the arrangement of FIG. 2 is illustrated in FIG. 6. In this modification, clamping sleeve 4' can be pressed into or glued into the outer sleeve 3'. Then, however, an additional part is required, namely a screw ring 22, which provides the required detent or stop in a pre-selected and pre-adjusted position. The positional independence when the parts are assembled is also established in this embodiment, however, it is not as advantageous as the embodiment shown in FIG. 2, because the pre-adjustment in the embodiment of FIG. 2 is established without influencing the gap which exists between the pressure cover 6 and the ram 9.

The recesses 18 can, advantageously, be formed in that the end face at the first end of the clamping sleeve 4 is approached from above with a cylindrical miller having a transverse disposed axis or in that it is milled in a long, slot plane with an arbitrary profile cutter having a rotational axis proceeding transverse relative to the slot plane. A circular shape is not absolutely necessary for the recesses 18, and the only thing critical is that as much material as possible is removed from the clamping sleeve 4 itself in the region of the slots so that only a line contact at the corresponding cooperating cone 20 of the clamping sleeve occurs with the cone 21 of the ram entering into the first end of the clamping sleeve. With only a line contact, the disengagement forces can be reduced to a minimum. This line contact forms only a fraction of the contacting circumference. Instead of being produced by milling and boring, the slot 16, aperture 17 and recess 18 can also be produced in a suitable way with an erosion process.

In comparison to the prior art, the embodiment described above has the advantage that the overall clamping device is constructed of only three parts, namely the outer sleeve 3, the clamping sleeve 4 and the ram 9.

An embodiment of the socket is generally indicated at 100' in FIG. 7. In this embodiment, a clamping sleeve 25 has a collar 26 at a second end which collar 26 has outside threads 29. An outer sleeve 28 at a second end has internal threads 30, and the clamping sleeve 25 is inserted into the second end of the outer sleeve 28 with the threads 29 received in the threads 30. After the clamping sleeve 25 is positioned, it is then secured against rotation. This can occur with one or more gluing or welding spots. For example, one or more access bores 41 are provided in the circumference of the outer sleeve 28 through which a welding or gluing can occur.

As in the first embodiment, the clamping sleeve 25 is provided with longitudinal slots 31 on both sides, and these longitudinal slots 31 end in recesses or apertures, such as 32. Lying diametrically opposite each other and offset by approximately 90° from the slots 31, the clamping sleeve 25 contains two grooves with conical seating surfaces 33, which correspond with the likewise conical or tapered mating surfaces 34 on projections 36 (FIG. 8), which projections extend from a lower end of a sleeve-shaped ram 35. The ram 35 also includes a step 37, with which the ram is axially seated against an inside collar or flange 38 at the first end of the outer sleeve 28. The coaction between the inside collar 38 and the step 37 forms an axial detent that insures that the two continuations or projections 36 of the ram 38 provided with the conical outside surfaces 34 remain engaged in the grooves forming the conical seating surfaces 33. The position of the ram 35 and the clamping sleeve 25 is adjusted only once during assembly of the ram and clamping sleeve, and are aligned relative to one another by insertion into the outer sleeve 28 proceeding from the second or tool side of the outer sleeve. The depth that the clamping sleeve 25 is threaded into the sleeve 28 will determine the degree of pre-adjustment of the tongues of the clamping sleeve. In this embodiment, too, the two cones or, respectively, conical seating surfaces 33 and 34 are designed so that only a line contact is established therebetween, for example at the location 39 in FIG. 9. This line contact remains practically unaltered during the disengagement action.

As illustrated in FIGS. 2 and 7, the opening 17 and 32, in which the longitudinal slots 16 and 31 extent, can have different designs and shapes. The shape as shown in FIG. 6 is especially advantageous. The recess therein is formed by tangential connections of two axially-spaced circles K1 and K2, which have different diameters. A particular advantage of this type of recess lies in the fact that a uniform course of material tension is established for the resilient tabs or tongues.

Although various minor modifications may be suggested by those versed in the art, it should be understood that we wish to embody within the scope of the patent granted hereon all such modifications as reasonably and properly come with the scope of our contribution to the art.

We claim:

1. A socket for clamping a cylindrical shaft of a dental tool, said socket having an outer sleeve, a clamping sleeve, and a displaceable ram, said outer sleeve having means for mounting the socket for rotation in a housing, said ram being inserted in said outer sleeve and being freely, axially displaceable between a position adjacent a first end of the outer sleeve and an inwardly disposed position that is closer to a second end of said outer sleeve, said ram having outer tapering surfaces extending at an angle to the axis of said outer sleeve on an end of the ram pointing towards said second end of said outer sleeve, said clamping sleeve having longitudinal slots extending inward from a first end to form resilient tongues, each of said tongues having an inner tapering surface extending at an angle to the axis of the clamping sleeve, said clamping sleeve being inserted into the outer sleeve with the first end of the clamping sleeve adjacent the outer tapering surfaces of said ram, means for securing the clamping sleeve in an axially immobile position in the outer sleeve, said ram being moved from a retracted position towards the clamping sleeve with the tapering surface of the ram coacting with the tapering surfaces of the tongues to urge the tongues from a closed position on a shaft of a tool inserted in the clamping sleeve to a radially outward unclamping position to release said tool, said angle of the outer tapering surfaces being greater than the angle of the inner tapering surfaces so that the contact between tapering surfaces of each tongue and ram form substantially a line contact with one another that is offset from the slots while in the unclamping position.

2. A socket according to claim 1, wherein the clamping sleeve has two diametrically opposed longitudinal slots and the inner tapering surfaces of the tongues are arranged offset by 90° relative to a plane of the slots.

3. A socket according to claim 1, wherein the ram is rotationally symmetrical to the axis and the tapering surface of the ram are formed by a conical surface, said clamping sleeve having two longitudinally extending slots lying in the same plane and terminating in recesses adjacent the first end of the clamping sleeve, said tapering surfaces of each tongue being a partial conical surface being offset relative to the plane of said two slots.

4. A socket according to claim 3, wherein each of the recesses at the first end of the clamping sleeve have a shape so that the resilient tongues have a decreasing width from the end of the slot to the first end of the clamping sleeve.

5. A socket according to claim 4, wherein each of the recesses at the first end of the clamping sleeve have a shape corresponding to a cylinder milled from the first end of the clamping sleeve with an axis of the cylinder extending transverse to the axis of the sleeve and lying in the plane of said slots.

6. A socket according to claim 4, wherein each of the recesses corresponds to a milled out portion produced in the plane of the slots with a profile cutter having a rotational axis extending transverse relative to the plane.

7. A socket according to claim 4, wherein the recesses are milled out portions.

8. A socket according to claim 4, wherein the recesses are formed by eroding portions out of said clamping sleeve.

9. A socket according to claim 1, wherein the angle of taper for the ram is approximately 30° to the axis of the socket and the angle of taper for the tongues is approximately 18° to the axis of the socket.

10. A socket according to claim 1, wherein the ram has two axially extending projections lying diametrically opposite one another, said outer tapering surfaces of said ram being on the outer portions of said projections and said clamping sleeve having two diametrically opposite inner grooves forming the inner tapering surfaces for coacting with the outer tapering surfaces of the ram.

11. A socket according to claim 10, wherein the outer sleeve adjacent the first end has an inwardly extending flange for retaining the ram in the sleeve, and said means for securing the clamping sleve in the outer sleeve includes a screw connection adjacent a second end of said clamping sleeve.

12. A socket according to claim 1, wherein a second end of the clamping sleeve is provided with threads forming the means for securing the clamping sleeve in the outer sleeve and the outer sleeve adjacent the first end hass inwardly extending shoulders engaging the ram to hold the ram within said sleeve.

13. A socket according to claim 1, wherein the clamping sleeve adjacent the first end has curved contact faces having a diameter slightly smaller than a diameter of the shaft of the tool to be held in said socket.

14. A socket according to claim 1, wherein said socket is mounted in a head housing of a dental handpiece for rotation, said second end of the outer sleeve and the clamping sleeve being positioned adjacent a surface of the housing facing towards the tool extending from the head housing of the dental handpiece.

15. A socket according to claim 14, wherein the first end of the outer sleeve is positioned adjacent a push button on the head housing, said push button having a projection for engaging an end of the ram opposite the outer tapering surfaces to urge the ram to a position to disengage the tongues of the clamping sleeve.

16. A socket according to claim 14, wherein the means for securing the clamping sleeve in the outer sleeve comprises a thread connection and said clamping sleeve has engagement means adjacent a second end for receiving an auxiliary tool for the purpose of assembling the clamping sleeve in said outer sleeve.

* * * * *